United States Patent [19]

Schaub

[11] Patent Number: 4,849,439
[45] Date of Patent: * Jul. 18, 1989

[54] α-PHENYL-α-CYCLOPROPYLALKYENE-1H-IMIDAZOLE- AND 1,2,4 TRIAZOLE-ETHANOLS AS ANTIMYCOTIC AGENTS

[75] Inventor: Fritz Schaub, Aesch, Switzerland

[73] Assignee: Sandoz Ltd., Basel, Switzerland

[*] Notice: The portion of the term of this patent subsequent to May 12, 2004 has been disclaimed.

[21] Appl. No.: 28,453

[22] Filed: Mar. 20, 1987

Related U.S. Application Data

[62] Division of Ser. No. 584,161, Feb. 27, 1984, Pat. No. 4,664,696.

[30] Foreign Application Priority Data

Mar. 4, 1983 [CH] Switzerland ............... 1196/83

[51] Int. Cl.$^4$ ............... A61K 31/41; C07D 249/08
[52] U.S. Cl. ............... 514/383; 514/184; 548/101; 548/262; 548/341
[58] Field of Search ............... 548/101, 262; 514/184, 514/383

[56] References Cited

U.S. PATENT DOCUMENTS

| 4,414,210 | 11/1983 | Miller et al. | 548/262 |
| 4,432,989 | 2/1984 | Spencer | 514/399 |
| 4,507,140 | 3/1985 | Sugarman | 548/262 |
| 4,664,696 | 5/1987 | Schaub | 548/262 |

FOREIGN PATENT DOCUMENTS

| 2064520 | 6/1981 | United Kingdom | 548/262 |
| 0048548 | 3/1982 | United Kingdom | 548/262 |

Primary Examiner—Richard L. Raymond
Assistant Examiner—Patricia L. Morris
Attorney, Agent, or Firm—Gerald D. Sharkin; Richard E. Vila

[57] ABSTRACT

The invention provides novel α-aryl- or -aralkyl-α-(cycloalkyl-alkyl)-1H-azole-1-ethanols, in which the alkyl moiety linking the cycloalkyl group to the ethanol group is substituted or branched at the carbon atom adjacent to the C(OH) group, which are useful as plant fungicides and for treating fungus diseases in man and animals. Other objects of the invention are plant fungicidal, pharmaceutical and veterinary compositions comprising such novel compounds and methods of combatting phytopathogenic fungi or fungus diseases with the aid of said novel compounds.

6 Claims, No Drawings

α-PHENYL-α-CYCLOPROPYLALKYENE-1H-IMIDAZOLE- AND 1,2,4 TRIAZOLE-ETHANOLS AS ANTIMYCOTIC AGENTS

This is a division of application Ser. No. 584,161, filed Feb. 27, 1984, now U.S. Pat. No. 4,664,696.

The invention relates to α,α-disubstituted-1H-azole-1-ethanols, more specifically to α-aryl- or -aralkyl-α-(cycloalkyl-alkyl)-1H-azole-1-ethanols.

The UK Patent Application 2,064,520 A discloses α-phenyl-α-($C_{3-8}$-cycloalkyl-$C_{1-3}$alkyl)-1H-1,2,4-triazole-1-ethanols having fungicidal activity. According to said application the preferred cycloalkyl-alkyl significance is $C_{3-6}$cycloalkyl-methyl; specific examples are given for the α-cyclohexylmethyl and α-cyclopentylmethyl significances.

It has now been found that α-aryl- or -aralkyl-α-(cycloalkyl-alkyl)-1H-azole-1-ethanols, in which the alkyl moiety linking the cycloalkyl group to the ethanol group is substituted or branched at the carbon atom adjacent to the C(OH) group, have surprisingly favourable fungicidal and pharmacological properties, particularly when its cycloalkyl is cyclopropyl.

The invention provides novel α-[aryl(alkylene)$_m$]-α-[$CR_1R_2$-$(CHR_3)_n$-$R_4$]-1H-1,2,4-triazole- and -1H-imidazole-1-ethanols, wherein $R_1$ is $C_{1-5}$alkyl, unsubstituted or substituted by halogen, by $C_{1-5}$-alkoxy, by phenyl-$C_{1-3}$alkoxy, by phenoxy, by $C_{1-5}$alkylthio, by phenyl-$C_{1-3}$alkylthio or by phenylthio, whereby optional phenyl groups may be substituted by $C_{1-5}$alkyl, halogen, halogen substituted $C_{1-5}$alkyl, $C_{1-5}$alkoxy or halogen substituted $C_{1-5}$alkoxy; or is $C_{2-5}$alkenyl or $C_{2-5}$alkinyl, unsubstituted or substituted by halogen or is cycloalkyl, unsubstituted or substituted by $C_{1-5}$alkyl or is phenyl, unsubstituted or substituted by substituents selected from the group consisting of halogen and $C_{1-5}$alkyl, $R_2$ and $R_3$, independently, are H or have an $R_1$ significance, whereby $R_1$ and $R_2$ may be linked together to form a $C_{3-7}$cycloalkyl group, m is 0 or 1, n is 0, 1 or 2, and $R_4$ is $C_{3-7}$cycloalkyl, unsubstituted or substituted by $C_{1-5}$alkyl, and ethers and esters of these ethanols (hereinafter compounds of the invention) and their use.

The aryl portion in the α-[aryl(alkylen)$_m$] moiety of the compounds of the invention is conveniently an aromatic hydrocarbon (e.g. naphthyl, preferably phenyl) unsubstituted or substituted, or an heteroaromatic ring linked via one of its ring carbon atoms (e.g. a 5- or 6-membered ring with 1 or 2 heteroatoms from the group O, N and S, preferably furyl, thienyl or pyridyl), unsubstituted or substituted.

Examples of suitable α-[aryl(alkylene)$_m$] groups are phenyl, benzyl and α-$C_{1-5}$alkylbenzyl, unsubstituted or mono- or multiple-substituted in the phenyl moiety by $NO_2$; halogen; $C_{1-5}$alkyl, $C_{2-5}$alkenyl, $C_{2-5}$alkinyl or $C_{1-5}$-alkoxy, unsubstituted or halogenated; phenyl or phenoxy, unsubstituted or substituted. Further examples of suitable α-aryl groups are the heteroaromatic 3-pyridyl group and 2-thienyl and 2-furyl unsubstituted or monosubstituted by halogen or lower alkyl (e.g. 5-Cl-2-thienyl and 5-tert.-butyl-2-furyl).

The α-[aryl(alkylene)$_m$] group is preferably phenyl, benzyl and α-$C_{1-5}$alkylbenzyl substituted in the phenyl moiety by $R_5$, $R_6$ und $R_7$ whereby $R_5$ and $R_6$, independently, are H; halogen; $C_{1-5}$alkyl, $C_{2-5}$alkenyl, $C_{2-5}$alkinyl or $C_{1-5}$alkoxy, unsubstituted or halogenated; phenyl or phenoxy, unsubstituted or substituted; or $NO_2$ and $R_7$ is H, $C_{1-5}$alkyl or halogen.

Any $C_{1-5}$alkyl moiety (substituent or part thereof) of the compounds of the invention has preferably 1 to 4, more preferably 1 or 2, particularly 1 carbon atom.

Any cycloalkyl group in the compounds of the invention is preferably 3- to 5-membered, particularly 3-membered.

Any halogen in the compounds of the invention is selected from F, Cl, Br and I.

Examples of preferred $C_{2-5}$alkenyl and $C_{2-5}$alkinyl singificances of $R_1$ are $CH_2$—CH=$CH_2$ and $CH_2$—C≡CH; suitable examples of halogenated derivatives thereof are especially monohalogenated groups such as $CH_2$—C≡CCl and $CH_2$—C≡CBr.

Preferred $C_{2-5}$alkenyl and $C_{2-5}$alkinyl significances of $R_5$ and $R_6$ are CH=$CH_2$ and C≡CH; suitable examples of halogenated derivatives thereof are particularly monohalogenated derivatives thereof, such as CCl=$CH_2$.

Examples of favourable phenyl substituents $R_5$ and $R_6$ are $CH_3$, F, Cl, Br, I, $CH_3O$, $C_6H_5$, $CF_3O$ and $C_2H_5$, particularly $CH_3$, $C_6H_5$ and especially Cl. In general the phenyl substituents are preferably in 2,4-position (e.g. 2,4-di-Cl), more preferably in 4-position (monosubstitution).

$R_7$ is preferably H.

n is preferably 0 or 1.

Where the hydroxy group of the compounds of the invention is etherified, such ethers are e.g. $C_{1-5}$alkyl, $C_{3-5}$alkenyl, $C_{3-5}$alkinyl or aralkyl ethers such methyl, allyl, propargyl or benzyl ethers; where such hydroxy group is esterified, the esters are e.g. esters of aliphatic carbon acids, such as the acetate.

The compounds of the invention contain one or more chiral centers. Such compounds are generally obtained in the form of racemic, diastereomeric and/or cis/trans mixtures. However, such mixtures can, if desired, be separated either completely or partly into the individual compounds or desired isomer mixtures by methods known in the art.

A preferred group of compounds of the invention is of formula I

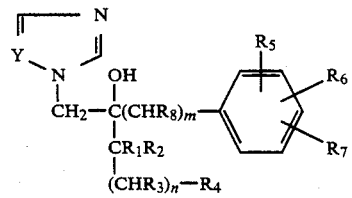

wherein $R_1$, $R_2$, $R_3$, $R_4$, $R_5$, $R_6$, $R_7$, m and n are as defined above, $R_8$ is H or $C_{1-5}$alkyl, and Y is CH or N and ethers and esters thereof.

The compounds of the invention can exist in free base form, in salt form, as acid addition salt with an organic or inorganic acid such as hydrochloride, or as alcoholate e.g. as Na ethanolate, and in metal complex form, e.g. with a metal from the groups Ib, IIa, IIb, VIb, VIIb, and VIII of the periodic table, such as copper and zinc, and with anions such as chloride, sulphate and nitrate.

The compounds of the invention are prepared by reaction of a compound of formula II

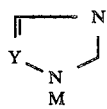

wherein
M is H, a metal or a trialkylsilyl group and
Y is defined above,
with a 2-[aryl(alkylen)$_m$]-2-[CR$_1$R$_2$-(CHR$_3$)$_n$R$_4$]-oxirane compound, wherein R$_1$, R$_2$, R$_3$, R$_4$, m and n are as defined above, or with a reactive functional derivative thereof, followed, where desired, by etherification or esterification of the thus obtained ethanol compounds.

Accordingly, the compounds of formula I are obtained by reaction of a compound of formula II with a compound of formula III

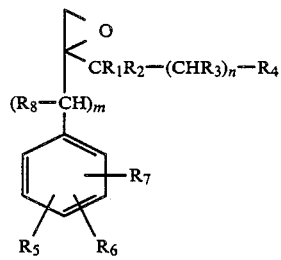

wherein R$_1$, R$_2$, R$_3$, R$_4$, R$_5$, R$_6$, R$_7$, R$_8$, m and n are as defined above or a reactive functional derivative thereof, followed, where desired, by etherification or esterification of the thus obtained ethanol compounds.

The process of the invention can be effected under conditions analogous to that known for the preparation of azole-1-ethanols by reaction of an azole with an oxirane.

Where in formula II M is H, the reaction with the oxirane compound is suitably effected in the presence of a base.

Where in formula II M is a metal, it is preferably an alkalimetal, e.g. Na.

Where in formula II M is trialkylsilyl e.g. trimethylsilyl the reaction is conveniently effected in the presence of a base such as NaH.

The process of the invention is conveniently effected in a solvent which is inert under the reaction condition, e.g. in dimethylformamide. A suitable reaction temperature is between ambient temperature and reflux temperature of the reaction mixture; where in the formula II M is trialkylsilyl it is conveniently higher than ambient temperature, e.g. between 70° and 90° C.

The term "reactive functional derivative" used in connection with the above 2-[aryl(alkylen)$_m$]-2-[CR$_1$R$_2$-(CHR$_3$)$_n$R$_4$]-oxiranes, such as the compounds of formula III, is intended to embrace any oxirane derivative that, by reaction with an azole of formula II results in ethanol compounds of the invention. Various examples of such reactive derivatives are known to a person skilled in the art; a suitable example thereof are the corresponding halohydrines (wherein the halogen is e.g. Cl or Br).

The conditions at which the compounds of formula II may be reacted with the reactive functional derivatives of the above defined 2-[aryl(alkylene)$_m$]-2-[CR$_1$R$_2$-(CHR$_3$)$_n$R$_4$]-oxiranes are also known per se. The reaction of a compound of formula II with the halohydrine derivative of a compound of formula III, can be effected under the conditions disclosed for the reaction with the oxirane compounds, conveniently, however, in the presence of an additional equivalent of a base.

Ester and ether derivatives of the ethanol compounds of the invention may be obtained according to known esterification and etherification procedures starting from the corresponding ethanols.

The compounds of the invention are obtained in free base form or is salt (acid addition salt or alcoholate) or metal complex form. The salt or metal complexes may be obtained from the corresponding free form in conventional manner and vice versa.

The compounds of the invention may be isolated from the reaction mixture and purified according to methods known per se.

Insofar as the preparation of the starting materials is not described, those are known or may be obtained according to resp. analogous to procedures described herein or to known procedures.

The compounds of the invention possess interesting biological, particularly antimycotic properties and are therefore indicated to be suitable for use as drug in the treatment of fungus diseases of humans and other animals. The antimycotic activity can be established by in vitro tests, e.g. the in vitro series dilution test on various families and species of mycetes, such as yeasts, mold fungi and dermatophytes at concentrations of about 0.05 to about 50 μg/ml and also by in vivo tests, e.g. by systemic, p.o. application of dosages of ca. 3 to 100 mg/kg body weight to mice which have been intravaginally infected with Candida albicans.

For the above mentioned use, the dose administered will, of course, vary depending on the compound employed, mode of administration and treatment desired. However, in general, satisfactory results are obtained when administered at a daily dosage of from 1 to 100 mg/kg of animal body weight, conveniently given in divided doses two to four times daily, or in sustained release form. For larger mammals having an approximate body weight of 70 kg the corresponding daily dosage are for example in the range of from 70 to 2000 mg; dosage forms suitable for e.g. oral administration comprise then from 17.5 to 1000 mg of active ingredient.

The compounds of the invention may be prepared and used in the free base form or in the form of pharmaceutically (resp. veterinary) acceptable salts (acid addition salts or alcoholates) or metal complexes. In general the salt forms exhibit the same order of activity as the free base forms. Acids that may be used in preparing acid addition salt forms include by way of illustration hydrochloric, hydrobromic, sulphuric, nitric, fumaric and naphthaline-1,5-disulphonic acids.

The compounds of the invention may be admixed with conventional pharmaceutically (resp. veterinary) acceptable inert carriers, and, optionally, other excipients. They may be administered in such internally administrable unit dosage forms as tablets or capsules, or alternatively be administered topically in such conventional forms as ointments or creams or parenterally. The concentrations of the active substance will, of course, vary depending on the compound employed, the treatment desired and the nature of the form etc. In general, however, satisfactory results are obtained e.g. in topical application forms at concentrations of from 0.05 to 5, in particular 0.1 to 1 wt %.

The compounds of the invention may be used in a manner analogous to that known for the use of standard compounds, such as ketoconazol. Particularly the compounds of formula I having one or more of the following features show useful pharmacological activity.

Y is N
m is 0
n is 0
$R_1$ is $CH_3$
$R_2$ is H or $CH_3$
$R_4$ is cyclopropyl
$R_5$ is in 4-position
$R_6$ is H or 2-Cl An appropriate daily dosage for a given compound of the invention will depend on various factors, e.g. its relative activity. This has for example been established for 2-(4-chlorophenyl)-3-cyclopropyl-3-methyl-1-(1H-1,2,4-triazol-1-yl)butan-2-ol at the model of the vaginal candidasis of the mouse and resulted in a recovery after oral application of $4 \times 50$ mg and even of $4 \times 5$ mg/kg body weight. The compounds of the invention may therefore be used in dosages analogous to that generally used for ketoconazol.

The compounds of the invention in free form or in agriculturally acceptable salt (acid addition salt or alcoholate) or metal complex form are also useful as fungicides in the combatting of phytopathogenic fungi. Their advantageous fungicidal activity is established by in vivo tests with test concentrations of from about 0.0008 to 0.05% against Uromyces appendiculatus (bean rust) on pole beans, against other rusts fungi (such as Hemileia, Puccinia) on coffee, wheat, pelargonium, snapdragon, against *Erysiphe cichoracearum* on cucumber and against other powdery mildew fungi (*E. graminis f.sp. tritici, E. Graminis f.sp. hordei, Podosphaera leucotricha, Uncinula necator*) on wheat, barley, apple, grapevine. Further interesting activities are i.a. observed in vitro against *Ustilago maydis* with test concentrations of from about 0.8 to 200 ppm, in vivo against *Rhizoctonia solani* with test concentrations of from 10 to 160 ppm (calculated per volume substrate). Since these tests indicate also a good plant tolerance and a good systemic action, the compounds of the invention are indicated for treatment of plant, seeds and soil to combat phytopathogenic fungi e.g. Basidiomycetes, Ascomycetes and Deuteromycetes, particularly, Basidiomycetes of the order Uredinales (rusts) such as Puccinia spp, Hemileia spp, Uromyces spp; Ascomycetes of the order Erysiphales (powdery mildew) such as Erysiphe spp, Podosphaera spp, and Uncinula spp, and of the other Pleosporales such as Venturia spp; as well as Phoma, Rhizoctonia, Helminthosporium, Pyricularia, Pellicularia (=Corticium), Thielaviopsis and Stereum spp. Various compounds of the invention, e.g. the compound of Example 1 hereinafter, possess also a good botryticide activity.

The amount of the compound of the invention to be applied, will depend on various factors such as the compound employed, the subject of the treatment (plant, soil, seed), the type of treatment (e.g. drenching, sprinkling, spraying, dusting, dressing), the purpose of the treatment (prophylactic or therapeutic), the type of fungi to be treated and the application time.

In general, satisfactory results are obtained, if the compounds of the invention are applied in an amount of from about 0.005 to 2.0, preferably about 0.01 to 1 kg/ha, in the case of a plant or soil treatment; e.g. 0.04 to 0.125 kg of active ingredient (a.i.) per ha in crops such as cereals, or concentrations of 1 to 5 g of a.i. per hl in crops such as fruits, vineyards and vegetables (at an application volume of from 300 to 1000 l/ha—depending on the size or leaf volume of the crop—which is equivalent to an application rate of approximately 10–50 g/ha). The treatment can, if desired, be repeated, e.g. at intervals of 8 to 30 days.

Where the compounds of the invention are used for seed treatment, satisfactory results are in general obtained, if the compounds are used in an amount of from about 0.05 to 0.5, preferably about 0.1 to 0.3 g/kg seeds.

The term soil as used herein is intended to embrace any conventional growing medium, whether natural or artificial.

The compounds of the invention may be used in a great number of crops, such as soybean, coffee, ornamentals (i.a. pelargonium, roses), vegetables (e.g. peas, cucumber, celery, tomato and bean plants), sugarbeet, sugarcane, cotton, flax, maize (corn), vineyards, pomes and stone fruits (e.g. apple, pears, prunes) and are particularly appropriate for use in cereals (e.g. wheat, oats, barley, rice), especially in wheat, and in apples.

Compounds of the invention particularly appropriate for agricultural use are compounds of formula I having one or more of the following features:

Y is N
m is 0
$R_8$ is H
n is 0
$R_1$ is $CH_3$
$R_2$ is H or $CH_3$
$R_4$ is cyclopropyl
$R_5$ is in 4-position
$R_6$ is H or 2-Cl.

The invention also provides fungicidal compositions, comprising as a fungicide a compound of the invention in free form, or in agriculturally acceptable salt or metal complex form in association with an agriculturally acceptable diluent. They are obtained in conventional manner, e.g. by mixing a compound of the invention with a diluent and optionally additional ingredients, such as surfactants.

The term diluents as used herein means liquid or solid, agriculturally acceptable material, which may be added to the active agent to bring it in an easier or better applicable form, resp. to dilute the active agent to a usuable or desirable strength of activity. Examples of such diluents are talc, kaolin, diatomaceous earth, xylene or water.

Especially formulations used in spray form, such as water dispersible concentrates or wettable powders, may contain surfactants such as wetting and dispersing agents, e.g. the condensation product of formaldehyde with naphthalene sulphonate, an alkylarylsulphonate, a lignin sulphonate, a fatty alkyl sulphate, an ethoxylated alkylphenol and an ethoxylated fatty alcohol.

In general, the formulations include from 0.01 to 90% by weight of active agent, from 0 to 20% fungicidally acceptable surfactant and from 10 to 99.99% diluent(s). Concentrated forms of composition, e.g. emulsifiable concentrates, contain in general from about 2 to 90%, preferably from between 5 and 70% by weight of active agent. Application forms of formulation contain in general from 0.0005 to 10% by weight of a compound of the invention as active agent. Typical spray-suspensions may, for example, contain 0.0005 to 0.05, preferably 0.001 to 0.02% e.g. 0.001, 0.002 or 0.005% by weight of active agent.

In addition to the usual diluents and surfactants, the compositions of the invention may comprise further additives with special purposes, e.g. stabilisers, desactivators (for solid formulations, on carriers with an active surface), agents for improving the adhesion to plants, corrosion inhibitors, anti-foaming agents and colorants. Moreover, further fungicides with similar or complementary fungicidal activity, e.g. sulfur, chlorothalonil, dithiocarbamates such as mancozeb, maneb, zineb, propineb, trichloromethane-sulphenylphthalimides and analoges such as captan, captafol and folpet, benzimidazoles such as benomyl, or other beneficially-acting materials, such as insecticides may be present in the formulations.

Examples of the production of plant fungicide formulations are as follows (parts are by weight):

(a) Wettable Powder Formulation

10 Parts of a compound of the invention are mixed and milled with 4 parts of synthetic fine silica, 3 parts of sodium lauryl sulphate, 7 parts of sodium lignin sulphonate, 66 parts of finely divided kaolin and 10 parts of a diatomaceous earth until the mean particle size is about 5 micron. The resulting wettable powder is diluted with water before use to a spray liquor, which may be applied by foliar spray as well as by root drench application.

b. Granules

Onto 94.5 parts by weight of quartz sand in a tumbler mixer are sprayed 0.5 parts by weight of a binder (non-ionic tenside) and the whole thoroughly mixed. 5 Parts by weight of a compound of the invention are then added and thorough mixing continued to obtain a granulate formulation with a particle size in the range of from 0.3 to 0.7 mm. The granules may be applied by incorporation into the soil adjacent to the plants to be treated.

c. Emulsion Concentrate

10 Parts by weight of a compound of the invention are mixed with 10 parts by weight of an emulsifier and 80 parts by weight of isopropanol. The concentrate is diluted with water to the desired concentration.

d. Seed Dressing

45 Parts of a compound of the invention are mixed with 1.5 parts of diamyl phenoldecaglycolether ehtylene oxide adduct, 2 parts of spindle oil, 51 parts of fine talcum and 0.5 parts of colorant Rhodamin B. The mixture is ground in a contraplex mill at 10,000 rpm until an average particle size of less than 20 microns is obtained. The resulting dry powder has good adherance and may be applied to seeds, e.g. by mixing for 2 to 5 minutes in a slowly turning vessel.

The following examples further illustrate the present invention. All temperatures are in centigrade. Rf values are on silica-gel.

FINAL PRODUCTS

Example 1:
2-(Chlorophenyl)-3-cyclopropyl-1-)1H-(1,2,4-triazol-1-yl)-butan-2-ol Step 1

7.6 1-(4-Chlorophenyl)-2-cyclopropyl-propanone-1 are dissolved in 120 ml of dry toluene, added at ambient temperature to 28.6 g dodecyldimethylsulfoniummethylsulfate and the suspension is stirred for 15 minutes. Thereto are added 6.3 g pulverised KOH and the reaction mixture is stirred for 18 hours at 35°. The reaction mixture is cooled, poured onto ice and, after the addition of some dimethyl formamide, extracted with diethylether. The organic extracts are washed three times with water and then with saturated aqueous NaCl solution, dried over $MgSO_4$ and evaporated in vacuum. The thus obtained oily residue comprises 2-(4-chlorophenyl)-2-(1-cyclopropylethyl)oxirane (besides dodecylmethylsulfide and dodecene-1).

Step 2

The crude oxirane reaction product of Step 1 is added dropwise to a mixture of 4.2 g 1,2,4-triazole and 15.4 g $K_2CO_3$ in 80 ml dry dimethylformamide (DMF) at 90°, and the mixture stirred at 90° for 2 hours. After cooling, the reaction mixture is poured onto ice and extracted with diethylether, the organic extracts are washed with water and with saturated aqueous NaCl-solution, dried over $MgSO_4$ and freed of solvent in vacuum. Chromatography of the residue on silica-gel with hexane/ethylacetate gives an oily, colourless sirup (diastereomeric mixture) which crystallizes slowly. Recrystallisation of the crystallisate from hexane/$CH_2Cl_2$ yields the title compound in the form of diastereomeric mixture as colourless crystals of the m.p. 100°–101°. Rf values in the thin layer chromatogram (on a silica gel plate using ethylacetate as the mobile phase) are:

diastereomer A: Rf-value 0.30
diastereomer B: Rf-value 0.38

By repeated chromatography on silica gel with diethyl ether/acetone (99:1) and diethyl ether/ethylacetate 99:1 to 90:10, followed by crystallisation from hexane/$CH_2Cl_2$, the diastereomeric mixture is separated into the pure diastereomers:

Example 1A: diastereomer A: m.p. 109°–110°
Example 1B: diastereomer B: m.p. 125°–127°.

Example 1C

A mixture of 2.0 g p-toluenesulfonic acid monohydrate in 50 ml toluene, is concentrated to a volume of 5 ml. Thereto is added dropwise with stirring, and at room temperature a solution of 2.9 g 2-(4-chlorophenyl)-3-cyclopropyl-1-(1H-1,2,4-triazol-1-yl)-butan-2-ol (diastereomeric mixture) in 35 ml abs. toluene. The reaction mixture is left standing until crystallisation. After the addition of 20 ml diethylether to the crystallisate formed in the toluene, the mixture is stirred for 30 minutes, filtered off, washed with diethylether and dried at 60° under high vacuum, m.p. 170°–171°.

Analogous to the procedure of Example 1C the following salts of the diastereomeric mixture of the title compound of Example 1 are obtained.

Example 1D: hydrogenoxalate, m.p. 180°–182°
Example 1E: hydrochloride, m.p. 190°–200°

Example 2:
2-(4-Chlorophenyl)-3-cyclopropyl-3-methyl-1-(1H-1,2,4-triazol-1-yl)-butan-2-ol 1-(4-Chlorophenyl)-2-cyclopropyl-2-methyl-propan-1-one is reacted analogous to the procedure of Example 1 (Steps 1 and 2). The purification of the title compound is effected by crystallisation from hexane to give colourless crystals of m.p. 88°–90° (=racemate of the title compound).

Example 3

Analogous to the procedure of Example 1 (Step 2), the following compounds of formula I (Tables A and B hereinafter) are obtained by reaction of an azole with the desired oxirane.

TABLE A

| Ex. | $R_1$ | $R_2$ | (CHR$_3$)$_n$ | $R_4$ | $R_5, R_6, R_7$ | Y | m.p. |
|---|---|---|---|---|---|---|---|
| | | | (m = o) | | | | |
| 3.1 | CH$_2$—C≡CH | H | — | Cyclopropyl | 4-Cl | N | |
| 2 | " | CH$_3$ | — | " | " | N | |
| 3 | " | Cyclopropyl | — | " | " | N | |
| 4 | Cyclopropyl | H | — | " | " | N | 84–86° |
| 5 | " | H | — | " | " | CH | 171.5–173.5° |
| 6 | " | CH$_3$ | — | " | " | N | |
| 7 | " | " | — | " | " | CH | |
| 8 | C$_2$H$_5$ | H | — | " | " | N | |
| 9 | CH$_3$ | H | — | " | 4-CH$_3$S | N | |
| 10 | CH$_3$ | H | — | " | " | CH | |
| 11 | CH$_3$ | H | — | " | 4-CH$_3$ | N | |
| 12 | CH$_3$ | CH$_3$ | — | " | " | N | |
| 13 | CH$_3$ | CH$_3$ | — | " | " | CH | |
| 14 | CH$_3$ | CH$_3$ | — | " | 4-CH$_3$O | N | |
| 15 | CH$_3$ | CH$_3$ | — | " | " | CH | |
| 16 | CH$_3$ | H | — | " | 2,4-diCl | N | 113–117° |
| 17 | CH$_3$ | H | — | " | " | CH | |
| 18 | CH$_3$ | CH$_3$ | — | " | 2,4-diCl | N | 141–142° |
| 19 | CH$_3$ | H | — | " | 2-CH$_3$—4-CH$_3$S | N | |
| 20 | CH$_3$ | H | — | " | 4-CH$_2$=CH | N | |
| 21 | CH$_3$ | CH$_3$ | — | " | " | CH | |
| 22 | CH$_3$ | CH$_3$ | — | " | " | N | |
| 23 | CH$_3$ | H | — | " | 4-HC≡C | N | |
| 24 | CH$_3$ | CH$_3$ | — | " | " | N | |
| 25 | CH$_3$ | CH$_3$ | — | " | " | CH | |
| 26 | CH$_3$ | H | — | " | 4-CH$_2$=CCl | N | |
| 27 | CH$_3$ | CH$_3$ | — | " | " | N | |
| 28 | CH$_3$ | CH$_3$ | — | " | " | CH | |
| 3.29 | 2-CH$_3$—cyclopropyl | H | — | 2-CH$_3$—cyclopropyl | 4-Cl | N | |
| 3.30 | " | " | CH$_3$ | — | " | " | N |
| 3.31 | " | H | — | " | " | CH | |
| 3.32 | CH$_2$—C≡C—Br | C$_3$H$_5$[1] | — | C$_3$H$_5$ | " | N | |
| 3.33 | " | CH$_3$ | — | " | " | N | |
| 3.34 | CH$_2$—C≡C—J | CH$_3$ | — | " | " | N | |
| 3.35 | CH$_2$—S—CH$_3$ | CH$_3$ | — | " | " | N | |
| 3.36 | " | CH$_3$ | CH$_2$ | " | 2,6-diCl | N | |
| 3.37 | " | CH$_3$ | CH$_2$ | " | 2,6-diCH$_3$ | N | |
| 3.38 | " | C$_3$H$_5$ | CH$_2$ | " | 2,6-diCH$_3$ | N | |
| 3.39 | " | CH$_3$ | CH$_2$ | " | 4-Cl—2,6-diCH$_3$ | N | |
| 3.40 | CH$_2$—O—CH$_3$ | CH$_3$ | — | " | 2,4-diCl | N | |
| 3.41 | CH$_3$ | H | — | C$_5$H$_9$[2] | 4-Cl | N | |
| 3.42 | CH$_3$ | H | — | C$_6$H$_{11}$[3] | 4-Cl | N | |
| 3.43 | CH$_3$ | CH$_3$ | CH$_2$ | C$_3$H$_5$ | 4-Cl | N | |
| 3.44 | CH$_3$ | H | — | C$_3$H$_5$ | 4-Cl | CH | 95–96°[4] |
| 3.45 | CH$_3$ | H | — | C$_3$H$_5$ | 4-Cl | CH | 147–148°[5] |

[1]C$_3$H$_5$ = Cyclopropyl;
[2]C$_5$H$_9$ = Cyclopentyl;
[3]C$_6$H$_{11}$ = Cyclohexyl;
[4]diastereomeric mixture;
[5]diastereomer A.

TABLE B

| Ex. | $R_1$ | $R_2$ | (CHR$_8$)$_m$ | $R_5, R_6, R_7$ | Y |
|---|---|---|---|---|---|
| | (n = o; R$_4$ = Cyclopropyl; m = 1) | | | | |
| 3.46 | CH$_3$ | H | CH$_2$ | 4-Cl | N |
| 3.47 | CH$_3$ | CH$_3$ | CH$_2$ | 4-Cl | N |
| 3.48 | C$_3$H$_5$ | H | CH$_2$ | 4-Cl | N |
| 3.49 | CH$_3$ | H | CH(i-C$_3$H$_7$) | 4-Cl | N |

Example 4:
2-(4-Chlorophenyl)-2-(1-cyclopropyl-cyclopropyl)-1-(1H-1,2,4-triazol-1-yl)-ethan-2-ol Step 1

A suspension of 5.1 80% NaH in 50 ml abs. tetrahydrofuran (THF) is stirred under a blanket of nitrogen. Thereto are added dropwise, at room temperature, 13.3 g dimethylsulfoxide (DMSO) and thereafter, within 20 minutes, 13.5 g 4-chlorophenyl-(1-cyclopropyl-cyclopropyl)-ketone in 50 ml abs. THF. To the resulting green suspension is added, portionwise, 15.0 g trimethylsulfonium iodide. The suspension is stirred for 16 hours at room temperature and 3 hours at 50°, and is then cooled to 0°–5°. Then water is added dropwise and the reaction mixture—after completion of the exothermic reaction—extracted with diethylether.

The organic phase is washed 3 times with water and once with saturated aqueous NaCl solution, dried over $MgSO_4$ and evaporated in vacuum at 60°. The residue consists mainly of 2-(4-chlorophenyl)-2-(1-cyclopropyl-cyclopropyl)-oxirane.

Step 2

The crude oxirane (of Step 1) is reacted with 1,2,4-triazole analogous to the process of the Example 1, Step 2, to give after chromatography on silica gel and crystallisation from hexane/$CH_2Cl_2$, the pure title compound, m.p. 110°–112° (racemate form).

Example 5:
2-(4-Chlorophenyl)-3-cyclopropyl-2-methoxy-3-methyl-1-(1H-1,2,4-triazol-1-yl)-butane To a suspension of 0.8 g NaH 80% in 25 ml DMF are added dropwise, at room temperature, a solution of 7.64 g 2-(4-chlorophenyl)-3-cyclopropyl-3-methyl-1-(1H-1,2,4-triazol-1-yl)-butan-2-ol in 50 ml DMF. The reaction is stirred at 40° for 30 minutes. Then are added dropwise, at 50°, 3.76 g $CH_3I$. The mixture is stirred for 18 hours at 20°, then poured into one liter of water and extracted with $CH_2Cl_2$. The organic phases are washed with water, dried over $MgSO_4$ and concentrated by continuous flask evaporation. The title compound is then obtained by chromatography of the residue on silica gel (mobile phase diethylether/triethylamine 10:2) in the form of white crystals, m.p. 87°–89°.

Example 6:
2-(4-Chlorophenyl)-3-cyclopropyl-2-allyloxy-3-methyl-1-(1H-1,2,4-triazol-1-yl)-butane The title compound is obtained analogous to the procedure of Example 5, except that allylbromide is used instead of $CH_3J$ and that the reaction mixture is stirred for 18 hours at 70° instead of at 20°, m.p. 58°–60° (white crystals).

Example 7:
2-(4-Chlorophenyl-3-cyclopropyl-2-benzyloxy-3-methyl-1-(1H-1,2,4-triazol-1-yl)-butane The title compound is obtained analogous to the procedure of Example 6, except that benzylbromide is used instead of allylbromide, m.p. 130°–132° (white crystals).

Example 8:
2-(4-Chlorophenyl)-3-cyclopropyl-2-acetoxy-3-methyl-1-(1H-1,2,4-triazol-1-yl)-butane The title compound is obtained analogous to the procedure of Example 5, except that acetylchloride is used (instead of $CH_3J$) and that the reaction mixture is stirred for 24 hours at 70°. It crystallizes from diethylether; m.p. 117°–119° (yellow crystals).

INTERMEDIATES

Example 9:
1-(4-Chlorophenyl)-2-cycloprpoyl-propanone-1

15 g 4-Chlorophenylcyclopropylmethyl ketone, dissolved in 80 ml abs. DMF, are added dropwise to a suspension of 2.6 g 80% NaH in 30 ml DMF under a blanket of $N_2$, and the mixture stirred for 2 hours at 25°–35°. Thereto are added, dropwise within 15 minutes, at room temperature, and with cooling 15.3 g $CH_3I$, the mixture is stirred for 15 minutes at 25°–30° and, after the addtion of cold water, taken up in ether. The organic extracts are washed with water and with saturated aqueous NaCl solution, dried over $MgSO_4$, evaporated to give the crude title compound which is purified by chromatography on silica gel with hexane/ethylacetate 98:2.

4-Chlorophenyl-(cyclopropylmethyl)-ketone is obtained by Jones oxydation of the corresponding alcohol with $CrO_3$ in aqueous $H_2SO_4$/acetone solution.

Example 10:
1-(4-Chlorophenyl)-2-cyclopropyl-2-methyl-propanone-1

One proceeds analogous to Example 9, uses however, 2.4 equivalents of NaH and 3 equivalents of $CH_3I$ per equivalent of 4-chlorophenyl cyclopropylmethyl ketone. The title compound is chromatographed on silica gel with hexane fraction/ethylacetate (99:1), $n_D^{20} = 1.5390$.

Example 11:
4-Chlorophenyl-(1-cyclopropyl-cyclopropyl)-ketone

A suspension of 4 g 80% NaH in 40 ml abs. THF is stirred under a blanket of $N_2$. Thereto are added dropwise, under mild reflux, within 40 minutes, 23.3 g of 4-chlorophenyl-(cyclopropylmethyl)-ketone in 250 ml abs. THF. Then are slowly added, at 20°, 15.8 ml phenylvinylsulfoxide with the aid of a syringe (exothermic reaction) and the mixture is stirred for 2½ hours at 20°–30°. The resulting intermediate (sulfoxide) is then cyclised to the title compound by stirring for 18 hours under reflux. The reaction mixture is cooled to 0°–5°, 200 ml water are then added dropwise and the mixture is extracted with diethylether. The organic phase is washed 3 times with water and once with saturated aqueous NaCl solution, dried over $MgSO_4$ and evaporated at 60° in vacuum.

The pure title compound is obtained by chromatography of the residue on silica gel with hexane/ethylacetate (99:1); $n_D^{20} = 1.5605$.

The procedure of Example 11 may also be effected by replacing phenylvinylsulfoxide by e.g. phenylvinylsulfone or by dimethylvinylsulfonium salt.

Example 12

The title compound of Example 9 may also be obtained starting from 4-chloro-benzylcyanide by reaction with cyclopropyl-methyl-ketone in the presence of NaH, reduction of the resulting 1-(4-chlorophenyl)-1-cyano-2-cyclopropyl-propene-1 with Mg/$CH_3OH$/$NH_4Cl$ to 1-(4-chlorophenyl)-1-cyano-2-cyclopropyl-propane, followed by oxidation with $O_2$ of said cyano compound under alkaline conditions in the presence of a phase transfer catalysator. Depending on the situation (price, environment etc.) the process of this example may be preferred.

Biological Activity/Fungicidal Use

1. Greenhouse test results

The following test results (test methods according to the procedures disclosed in UK 2064520A) illustrate the surprisingly favourable fungicidal activity of the compounds of the invention. The standard is α-cyclohexyl-methyl-α-(p-methylphenyl)-1H-1,2,4-triazole-1-ethanol (Ex. 2Z-22 of UK 2064520A). Results are expressed in EC 90, i.e. the concentration allowing a 90% control of fungal disease, after spray application.

| Compound of Example | 1* | 2 | 3.16 | 3.18 | Standard |
|---|---|---|---|---|---|
| Fungus/crop | | | | | |
| Erysiphe/cucumber | 5 | 8 | 1 | <1 | 38 |
| Erysiphe/wheat | 3 | 4 | 5 | 3 | >900 |
| Podosphaera/apple | 6 | 5 | 5 | 3 | 126 |
| Uncinula/grape | 4 | 6 | 15 | 2 | 46 |
| Uromyces/bean | <1 | <1 | <1 | 1 | <30 |
| Septoria/wheat | 39 | 32 | 77 | 36 | >900 |

*diastereomeric mixture

2. Disease control under field conditions

The fungicidal activity of the compound of Example 1 was further evaluated under field conditions: 62 g a.i./ha allowed more than 90% control of powdery mildew and 90% control of rust infestation in cereals; and 2.6 g a.i./hl allowed up to 99% control of powdery mildew in vineyards.

Further evaluations indicate a fungicidal activity of the compound of Example 1 which is equivalent or better than propiconazol against powdery mildew in cereals and cucumbers and against rusts in cereals and coffee, resp.

equal to better than fenarimol against powdery mildew in apples and grapes, and against venturia in apples, resp.

better than triadimefon against i.a. rusts in coffee.

What we claim is:

1. A pharmaceutical or veterinary composition in capsule, tablet, topical ointment or topical cream form containing an inert pharmaceutically or veterinary acceptable carrier and an anti-mycotic effective amount of a compound of the formula:

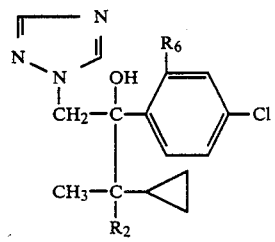

wherein
$R_2$ is H or $CH_3$, and
$R_6$ is H or chloro,
in free form or in acid addition salt, alcoholate or metal complex form.

2. A composition of claim 1 in which the compound is 2-(4-chlorophenyl)-3-cyclopropyl-3-methyl-1-(1H-1,2,4-triazol-1-yl)-butan-2-ol.

3. A composition of claim 1 in which the compond is 2-(4-chlorophenyl)-3-cyclopropyl-1-(1H-1,2,4-triazol-1-yl)-butan-2-ol.

4. A method of treating mycosis in man or animal which comprises administering internally or topically to the man or animal an anti-mycotic effective amount of a compound of the formula:

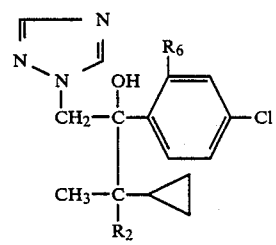

wherein
$R_2$ is H or $CH_3$, and
$R_6$ is H or chloro,
in free form or in acid addition salt, alcoholate or metal complex form.

5. The method of claim 4 in which the compound is 2-(4-chlorophenyl)-3-cyclopropyl-3-methyl-1-(1H-1,2,4-triazol-1-yl)-butan-2-ol.

6. The method of claim 4 in which the compound is 2-(4-chlorophenyl)-3-cyclopropyl-1-(1H-1,2,4-triazol-1-yl)-butan-2-ol.

* * * * *